(12) United States Patent
Hyoue

(10) Patent No.: US 8,920,454 B2
(45) Date of Patent: Dec. 30, 2014

(54) LANCET

(75) Inventor: Tomoyuki Hyoue, Maniwa (JP)

(73) Assignee: Asahi Polyslider Company, Limited, Osaka (JP)

( * ) Notice: Subject to any disclaimer, the term of this patent is extended or adjusted under 35 U.S.C. 154(b) by 1357 days.

(21) Appl. No.: 12/224,132

(22) PCT Filed: Feb. 19, 2007

(86) PCT No.: PCT/JP2007/052960
§ 371 (c)(1),
(2), (4) Date: Oct. 14, 2008

(87) PCT Pub. No.: WO2007/097283
PCT Pub. Date: Aug. 30, 2007

(65) Prior Publication Data
US 2009/0312781 A1 Dec. 17, 2009

(30) Foreign Application Priority Data

Feb. 20, 2006 (JP) ................................ 2006-042340

(51) Int. Cl.
*A61B 17/32* (2006.01)
*A61B 5/15* (2006.01)
*A61B 5/151* (2006.01)

(52) U.S. Cl.
CPC ........... *A61B 5/1411* (2013.01); *A61B 5/15142* (2013.01)
USPC ....................................................... 606/181

(58) Field of Classification Search
USPC ................... 606/181–183, 186–189; 600/583
See application file for complete search history.

(56) References Cited

U.S. PATENT DOCUMENTS

| 5,207,699 A | 5/1993 | Coe |
| 5,385,571 A | 1/1995 | Morita |

(Continued)

FOREIGN PATENT DOCUMENTS

| EP | 1 815 792 | 8/2007 |
| FR | 2 595 237 | 9/1987 |

(Continued)

OTHER PUBLICATIONS

International Search Report issued Mar. 13, 2007 in the International (PCT) Application of which the present application is the U.S. National Stage.

(Continued)

*Primary Examiner* — Ryan Severson
*Assistant Examiner* — Rachel S Papeika
(74) *Attorney, Agent, or Firm* — Wenderoth, Lind & Ponack, L.L.P.

(57) ABSTRACT

A lancet includes a lancet body having a distal end portion of a puncturing member protruding from the front end portion thereof, and a cap that houses and protects the distal end portion of the puncturing member that protrudes before use, wherein the front end portion of the lancet body and the rear end portion of the cap are integrated in substantially adjoining state with each other via a weakened portion. One of the end face at the front end portion of the lancet body and the end face at the rear end portion of the cap that opposes the former has protrusions, and the top ends of the protrusions define an imaginary plane that extends perpendicularly to the longitudinal direction of the puncturing member, and the other end face defines the flat surface that extends perpendicularly to the longitudinal direction of the puncturing member.

11 Claims, 5 Drawing Sheets

(56) References Cited

U.S. PATENT DOCUMENTS

| | | | |
|---|---|---|---|
| 5,554,166 A * | 9/1996 | Lange et al. | 606/182 |
| 5,913,868 A * | 6/1999 | Marshall et al. | 606/181 |
| 2003/0199891 A1* | 10/2003 | Argauer | 606/181 |
| 2004/0068282 A1* | 4/2004 | Bicknell | 606/181 |
| 2005/0131440 A1 | 6/2005 | Starnes | |
| 2007/0162064 A1* | 7/2007 | Starnes | 606/181 |
| 2009/0275968 A1 | 11/2009 | Kitamura et al. | |

FOREIGN PATENT DOCUMENTS

| | | |
|---|---|---|
| JP | 5-285127 | 11/1993 |
| JP | 6-23505 | 3/1994 |
| JP | 9-266898 | 10/1997 |
| WO | 99/27855 | 6/1999 |
| WO | 2006/046570 | 5/2006 |
| WO | 2007/114101 | 10/2007 |

OTHER PUBLICATIONS

Supplementary European Search Report (in English language) issued Aug. 20, 2010 in corresponding European Patent Application No. 07 71 4486.

* cited by examiner (A)

(B)

LANCET

FIELD OF THE INVENTION

The present invention relates to a lancet used to take a small amount of a blood sample, and particularly to a disposal lancet.

DESCRIPTION OF THE RELATED ART

Lancets used to take blood sample include one, for example, disclosed in Japanese Utility Model No. 2,561,697, having the constitution schematically shown in perspective view of FIG. 1 and side view in FIG. 2. The lancet 10 comprises a lancet body 12 and a cap 14, wherein a distal end 18 of a needle protrudes as a puncturing member 16 from a front end portion 20 of the lancet body 12. Before the lancet is put into use, the protruding distal end portion 18 of the puncturing member 16 is embedded in a resin that constitutes the cap 14, while being sealed off the atmosphere around the lancet. Before use, the front end portion 20 of the lancet body and the rear end of the cap 14 are integrated with each other via a weakened portion 22.

In preparation for puncturing operation that uses the lancet described above, it is necessary to expose the distal end portion 18 of the puncturing member 16. For this purpose, the lancet body 12 and the cap 14 are twisted in directions opposite to each other around the puncturing member 16 (more precisely around an axis 24 in the longitudinal direction of the puncturing member), so as the break the weakened portion 22 formed from a resin. Then the lancet body 12 is separated from the cap 14, thereby exposing the distal end portion 18 of the puncturing member 16 from the front end portion 20 of the lancet body 12.

To carry out the puncturing operation, an injector is used to launch the lancet body 12 with the distal end portion 18 exposed, so that the distal end portion 18 punctures a predetermined portion of human body to prick and bleed.

When the above lancet is used for the puncturing operation, the person from whom blood sample being taken naturally feels a pain when the needle penetrates his (or her) skin. In order to relieve the pain as much as possible, it has been attempted to use finer needles. Nowadays, a stainless steel needle having a diameter of 0.2 mm (33 gauge) is used as the finest needle.

SUMMARY OF THE INVENTION

Problems to be Solved

When the weakened portion is twisted to break in order to use the lancet that employs such a fine needle as the puncturing member, it is very difficult to twist the lancet body 12 and the cap 14 around the puncturing member precisely in directions opposite to each other. In many cases, it was found that the direction in which the distal end portion of the puncturing member extends and the direction in which rest of the puncturing member extends fail to agree with each other, and the distal end portion of the puncturing member tends to bend near the end of the lancet body.

In such a case, even when it is assumed that the lancet body is launched by the injector in the direction in which the rest of the puncturing member extends, the distal end portion of the puncturing member is bent and therefore impinges on the human body in a significantly inclined direction, not at perpendicular angle or near to the skin surface of the area being punctured. As a result, the distal end portion of the puncturing member forcibly penetrates into the human body. When punctured in an inclined direction as described above, even when the lancet body moves in a direction perpendicular or near to the body surface and even if the fine needle is used as the puncturing member, movement of the needle to penetrate into the body tissue and withdraw thereafter receives a significant resistance from the tissue, because the distal end portion of the puncturing member is bent. This causes more pain to the subject person than in the case of puncturing in a direction perpendicular or substantially perpendicular to the body surface with a lancet having distal end portion of the puncturing member that is not bent.

Accordingly, a problem to be solved by the present invention is to provide a lancet in which the distal end portion 18 of the puncturing member does not easily bend when the weakened portion 22 between the lancet body 12 and the cap 14 is broken.

Means for Solving the Problem

It was found that the problems described above can be solved by a lancet that comprises a lancet body having a front end portion, from which a distal end portion of a puncturing member protrudes, and a cap that houses and protects the distal end portion of the puncturing member before use, wherein the front end portion of the lancet body and the rear end of the cap are integrated in a substantially adjoining state with each other via a weakened portion; one of an end face at the front end portion of the lancet body and an end face at the rear end portion of the cap that opposes the former has at least one protrusion and top ends of the protrusions define an imaginary plane that extends perpendicularly to the longitudinal direction of the puncturing member; and the other end face defines a flat surface that extends perpendicularly to the longitudinal direction of the puncturing member.

In the lancet of the present invention, the weakened portion is located between the front end portion of the lancet body and the rear end portion of the cap, and surrounds a part of the puncturing member that resides therein. In the lancet of the present invention, the flat surface or the imaginary plane defined by the end face at the front end portion of the lancet body extends perpendicularly to the longitudinal direction of the puncturing member. Positional relationship between the lancet body and the puncturing member can be easily realized by forming the lancet of the present invention by molding process, preferably by insertion molding process wherein the puncturing member is placed within a die before being molded. However, any other manufacturing method may also be employed as long as the above-mentioned relation can be ensured.

Advantageous Effect of the Invention

With the lancet of the present invention, the distal end portion of the puncturing member can be prevented from bending at the front end portion of the lancet body as much as possible. It is because when the lancet body is twisted relative to the cap in directions opposite to each other, the imaginary plane and the flat surface can be ensured to make sliding motion while substantially making contact with each other and rotating around the longitudinal axis of the puncturing member (therefore no inclination occurring from the state of contact), even when the imaginary plane and the flat surface would have inclined from each other without rotating in a state of being parallel to each other. The present invention is particularly advantageous for a lancet having a very fine puncturing member, specifically a lancet that employs a needle measuring 0.4 mm or less in diameter (diameter of a substantially cylindrical portion, not the distal end portion), particularly 0.25 mm or less, for example 34 gauge (0.18 mm in diameter) as the puncturing member.

DESCRIPTION OF REFERENCE NUMERALS

Figure 1:
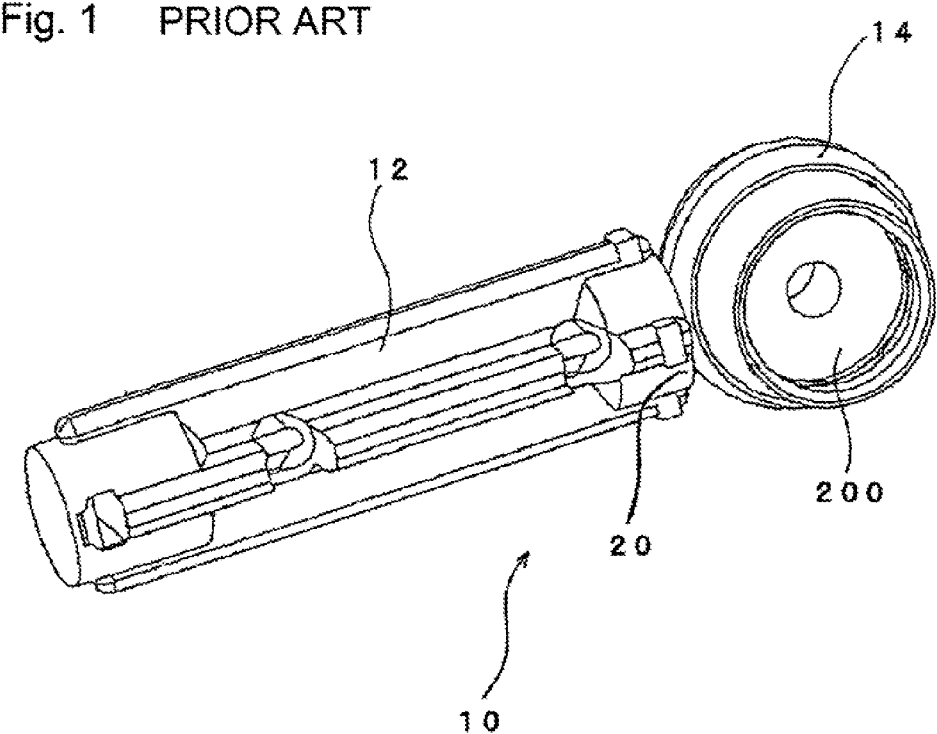
FIG. 1 is a schematic perspective view of a conventional lancet.
Figure 2:
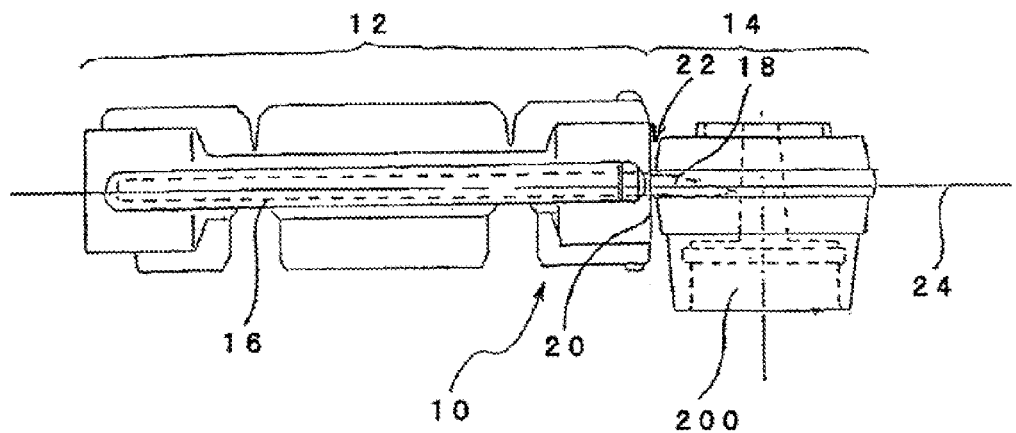
FIG. 2 is a schematic side view of the lancet shown in FIG. 1.

In the accompanying drawings, the reference numerals represent the following elements.
10 Lancet
12 Lancet body
14 Cap
20 Front end portion
22 Weakened portion
24 Longitudinal axis of puncturing member
100 Lancet
102 Lancet body
104 Cap
106 Puncturing member
108 Distal end portion
110 Rear end portion
112 Front end portion
114 Weakened portion
120 End face
122 End face
124 Base portion
126 Protrusion
128 Top end
130 Linkage
132 Imaginary plane
140, 142, 146, 148, 150, 152, 154 Ridges

DETAILED DESCRIPTION OF THE INVENTION

In one embodiment of the lancet of the present invention, a front end portion of the lancet body 12 and a rear end portion of the cap are in a state of adjoining each other (hence the length of the weakened portion is substantially zero), and the imaginary plane defined by the end faces of these members and the end faces extend in a direction substantially perpendicular to longitudinal direction of the puncturing member, namely the puncturing direction. In this embodiment, when the lancet body and the cap are twisted in directions opposite to each other around the puncturing member, it is ensured that the imaginary plane of one end face extends in a direction perpendicular to longitudinal direction of the puncturing member and that the flat surface of the other end face extend in a direction perpendicular to longitudinal direction of the puncturing member. As a result, the lancet body and the cap turn in directions opposite to each other, while the imaginary plane of one end face and the flat surface of the other end face maintain the substantially planar contact state. Accordingly, by simply twisting (or turning) the lancet body and the cap in directions opposite to each other around the longitudinal direction in preparation for the puncturing operation, it is made possible to twist the lancet body and the cap in directions opposite to each other around the axis of the puncturing member without need to pay particular attention to the positional relationship of these members.

In case bending of the puncturing member is permitted to some extent, the weakened portion that links the front end portion of the lancet body and the rear end portion of the cap into an integral configuration may have a substantial length along the longitudinal direction of the puncturing member, which causes the imaginary plane of one end face and the flat surface of the other end face to be separated from each other by a distance corresponding to the length. In this case, length of the weakened portion means the distance between the imaginary plane of one end face and the flat surface of the other end face.

While the length of the weakened portion may be suitably selected in accordance to the permitted extent of bend, the length is usually within 5 times the diameter of the puncturing member (the diameter of substantially cylindrical portion of the puncturing member), preferably 4 times the diameter, for example 3 or 2 times the diameter, more preferably the length equals to or less than the diameter, for example, equals to the diameter or 0.5 times thereof. In this case, strictly speaking, the front end portion of the lancet body and the rear end portion of the cap do not adjoin each other. However, when the lancet body and the cap are twisted in directions opposite to each other around the puncturing member, the imaginary plane of one end face and the flat surface of the other end face can maintain the state close to the planar contact state, even when these surfaces are not parallel but inclined to each other, and therefore distal end portion of the puncturing member 16 will not bend by a considerable angle.

As will be easily understood, since the lancet is capable of being twisted in such a state as the flat surface of the other end face is inclined by a certain angle relative to the imaginary plane of one end face, there is a possibility of the distal end portion of the puncturing member to bend by this inclination angle at the maximum. In actuality, the puncturing member formed from a metal such as stainless steel has elasticity and therefore usually would not bend to such a large angle as the maximum angle, when it is bent.

The adjoining state refers to the state in which length of the weakened portion is 0 times the diameter so that the imaginary plane of one end face and the flat surface of the other end face adjoin with each other, in such a configuration as the top end that defines the imaginary plane makes contact with the other end face, and are linked to each other. The portion being linked (i.e. the linkage) is made through a linear portion or a narrow elongated surface, and can be easily broken by twisting the lancet body and the cap each other, similarly to the weakened portion. In case the linkage has a thickness (dimension of the linkage in the puncturing direction), it becomes less easy to break. This embodiment corresponds to one where the weakened portion has a definite length. In the embodiment where the members are in adjoining state, the weakened portion and the linkage may be integrally connected with each other (see the embodiment shown in FIG. 3).

In the present specification, an expression "substantially adjoining state" will be used to collectively represent the case where length of the weakened portion is zero and the case where the weakened portion has a length up to five times the diameter of the puncturing member and, in this situation, an expression "substantially planar contact state" will be used to collectively represent the cases where the end faces or the flat surface defined by the end faces and the imaginary plane are in the state of planar contact and the state of substantially planar contact. In the latter case (substantially planar contact state), if the length of the weakened portion is restricted to one of the lengths described above in a range of up to five times the diameter of the puncturing member, the expression "substantially planar contact state" will be used to collectively represent a case where the length of the weakened portion is zero and a case where the weakened portion has such a small length.

In the lancet of the present invention, the end face that defines the imaginary plane may be either the end face at the front end portion of the lancet body or the end face at the rear end portion of the cap that opposes the former. That is, it may be that front the end face at the front end portion of the lancet body defines the imaginary plane and the end face at the rear end portion of the cap defines the surface, or the end face at front end portion of the lancet body 12 defines the flat surface and the end face at the rear end portion of the cap defines the imaginary plane (the embodiment shown in FIG. 3 to be described later). In another embodiment of the lancet of the present invention, the other end face defines the imaginary plane similarly to the "one end face" provided that the state of substantially planar contact can be maintained.

In the lancet of the present invention, the end face at the front end portion of the lancet body and/or the rear end portion of the cap has protrusions that protrude toward the other end face that opposes thereto, and top ends of the protrusions define the imaginary plane that extends perpendicularly to the longitudinal direction of the puncturing member. In general, such an end face is constituted from the protrusions and a flat portion that is not occupied by the protrusions (usually the base portion from which the protrusions protrude), and the latter portion will be referred to as the base of the end face in this specification. In one embodiment, the end face may be occupied by the protrusions as a whole (that is, the end face does not have a flat portion). In another embodiment, the end face may be constituted from protrusion(s) and a flat portion. The highest portion of the protrusion(s) defines the top end.

The imaginary plane means one single imagined plane that is surmounted on the top end(s) of the protrusion(s) and contacts therewith (or includes it), not a surface that actually exists. Mathematically, a plane can be defined by specifying three points that do not lie on the same straight line. Therefore, the imaginary plane defined by at least three top ends of the protrusions is perpendicular to the longitudinal direction of the puncturing member. It becomes easier to maintain the state of substantially planar contact between the imaginary plane of one end face and the flat surface of the other end face when twisting the lancet body and the cap in opposite directions, by increasing the number of top ends that define the imaginary plane.

When an end face defines an imaginary plane, at least three top ends, preferably more than three top ends of the protrusions have substantially the same height. The phrase "same height" means that the top ends of the protrusions lie on the same plane that is perpendicular to the puncturing member. In case the end face has top ends of different heights, the top end mentioned herein means the top end located at the highest position, and at least three top ends located at the highest position are necessary. In case the top end has a linear configuration, it is preferable that the top ends formed of two or more straight lines lie at substantially the same height. In case the top end has planar configuration, a single surface can define the imaginary plane in an ideal situation. However, since it is preferable that the top end having a planar shape is narrow in width, it is preferable that at least two top ends of narrow planar configuration are located at substantially the same height.

The protrusion may have any suitable shape. For example, a protrusion may have needle shape, rod shape, semi-sphere, cone, pedestal shape, ridge or wall (wall of straight, zigzag, curved (undulating, spiraling, circular, etc.) or other shape) protruding on the end face, or a combination of these shapes. In case the front end portion of the lancet body and the rear end portion of the cap are in the adjoin state (namely length of the weakened portion is zero), the protrusion needs to be broken along with the weakened portion and therefore preferably has the top end of smaller surface area. For example, a top end has a shape of dot, small circle, small triangle, rectangle or polygon, linear or narrow strip shape (such as thread or very narrow rectangle). In case the front end portion of the lancet body and the rear end portion of the cap are in substantially adjoining state (these members do not directly adjoin each other, or length of the weakened portion is not zero), it is not necessary to take into account the breakage thereof.

It is preferable that the end face, which includes the protrusions, defines a space that is open to the surrounding (in other words, it is not much preferable that the end face defines a closed space). It is particularly preferable to form the protrusion so as to define a space that does not narrow toward the outside from the center of the end face. This embodiment is advantageous in terms of mold releasing when manufacturing the lancet of the present invention from a resin by insertion molding or the like, as will be described later. However, since a resin has elasticity, it is possible to form a protrusion that defines a space that narrows toward the outside. The words "open" and "closed" are used here in relation to the longitudinal direction of the puncturing member.

In one preferred embodiment, the protrusion has a ridge shape. In this case, top ends of the ridge preferably define a linear shape or an elongated surface along with the longitudinal direction of the ridge. The ridge may have linear or curved shape as a whole, or a combination thereof. For example, a configuration of curved ridges running parallel to each other, straight ridges running parallel to each other or ridges having any shapes crossing each other may be employed. The protrusion may have a grating-like configuration constituted, for example, from a plurality of parallel ridges and one ridge that cross the former at right angles (or obliquely). In another embodiment, the protrusion may be constituted from a plurality of ridges that extend radially from a cylinder or a truncated cone (small in height and in diameter) that surrounds the puncturing member.

The lancet of the present invention, excluding the puncturing member, is preferably formed from a resin (for example, polyethylene, polypropylene, polystyrene, silicone, etc.) by molding, particularly injection molding, more particularly insertion molding where the puncturing member is placed in a die in advance. For the puncturing member, a needle made of stainless steel may be used. For the manufacture of the lancet of the present invention, a particularly fine needle, for example, 33 gauge or 34 gauge, may be used as the puncturing member. In consideration of mold release, it is preferable that the lancet of the present invention has the protrusion having a form such as ridge, that makes it easy to pull the die portion, that is used to form the protrusion that defines the imaginary plane, to the surrounding of the lancet. Specifically, such a configuration is preferably employed as straight ridges cross each other, preferably at right angles, or run in parallel to each other, or a combination of these (for example, a ridge crossing a plurality of parallel ridges). The end face that opposes the imaginary plane may be a flat surface or have a protrusion similarly to the imaginary plane.

Figure 3:
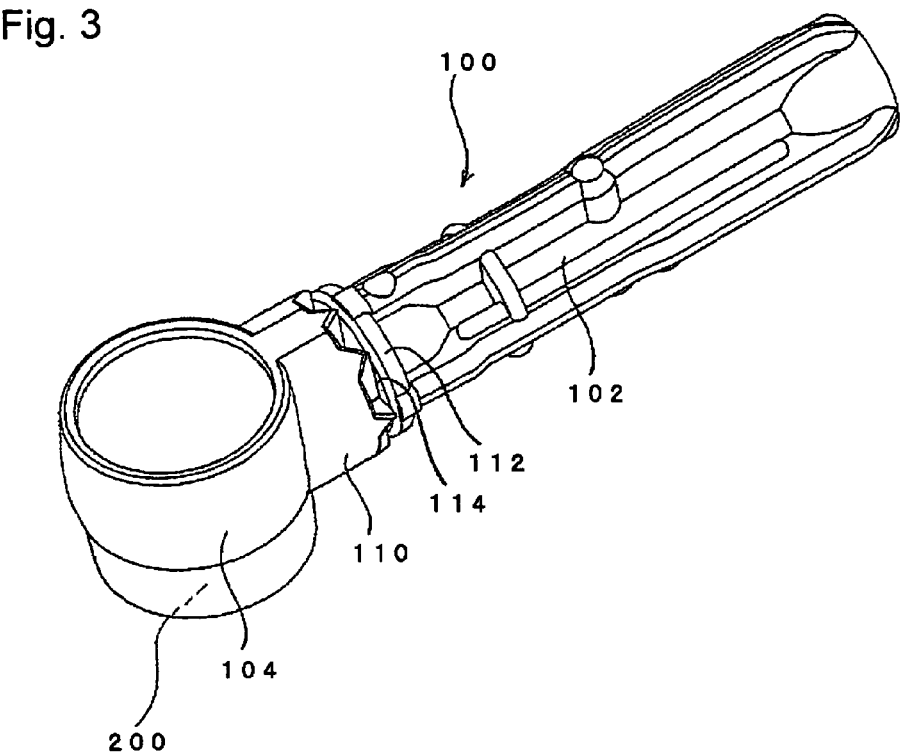
FIG. 3 is a schematic perspective view of an example of lancet according to the present invention.
Figure 4:
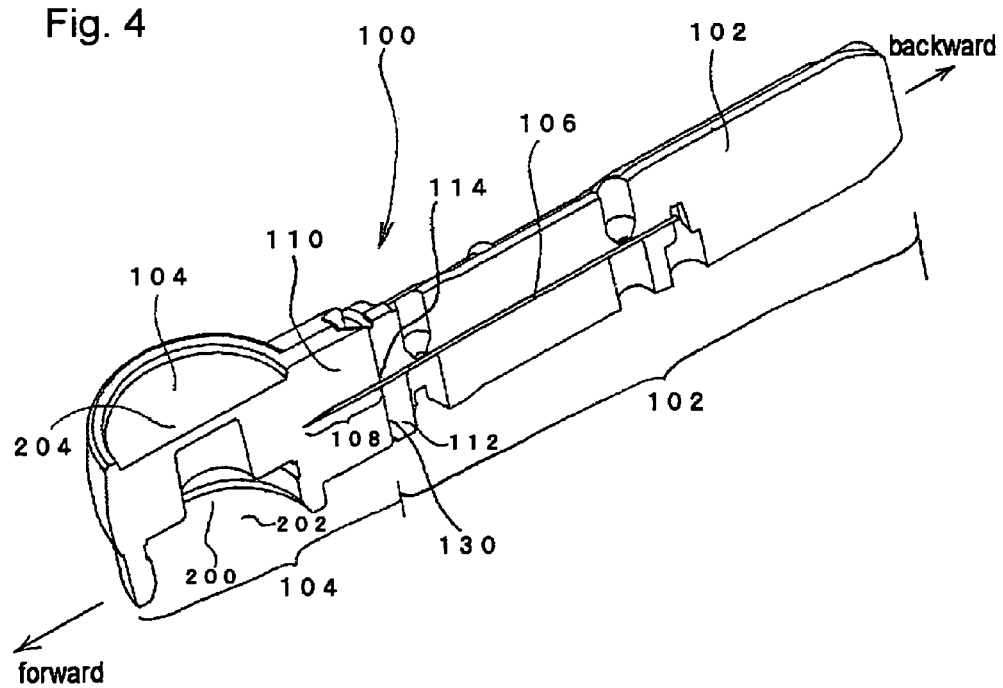
FIG. 4 is a schematic perspective view of a lancet according to the present invention shown in FIG. 3, with one half thereof on the proximal side being cut away.

An example of the lancet of the present invention is shown in schematic view of FIG. 3, and the lancet of the present invention shown in FIG. 3 is show with one half thereof on the proximal side being cut away in FIG. 4. The lancet 100 of the present invention comprises the lancet body 102 and the cap 104. The puncturing member 106 straddles the lancet body 102 and the cap 104, being disposed inside of these members substantially at the center, with the distal end 108 thereof housed in the cap 104.

In the embodiment shown, the rear end portion 110 of the cap 104 and the front end portion 112 of the lancet body 102 are integrated with each other via a weakened portion 114, in substantially adjoining state. In preparation for puncturing operation, the lancet body 102 and the cap 104 are twisted in directions opposite to each other around the puncturing member 106, so as to break the weakened portion 114 and separate the lancet body 102 from the cap 104. Then these members are brought away from each other along the longitudinal direction of the puncturing member 106, thereby exposing the distal end portion 108 of the puncturing member (refer to FIG. 5 and FIG. 6).

In the embodiment shown in the drawing, as will be described later, the lancet body 102 and the cap 104 are in adjoining state, while the top ends 128 of the protrusion that define the imaginary plane make contact with a flat surface 120 that is defined by the front end portion 112 of the lancet body 102, so as to form a linkage 130. As a result, when the weakened portion 114 is broken, the linkage 130 is broken at the same time.

Throughout this specification, the terms "front" and "rear" are used in reference to the direction in which the lancet moves during puncturing operation. Accordingly, the lancet 100 moves toward the front direction until the exposed distal end portion 108 of the puncturing member punctures a predetermined position, and moves toward the rear direction thereafter (refer to the arrow in FIG. 4).

Figure 5:
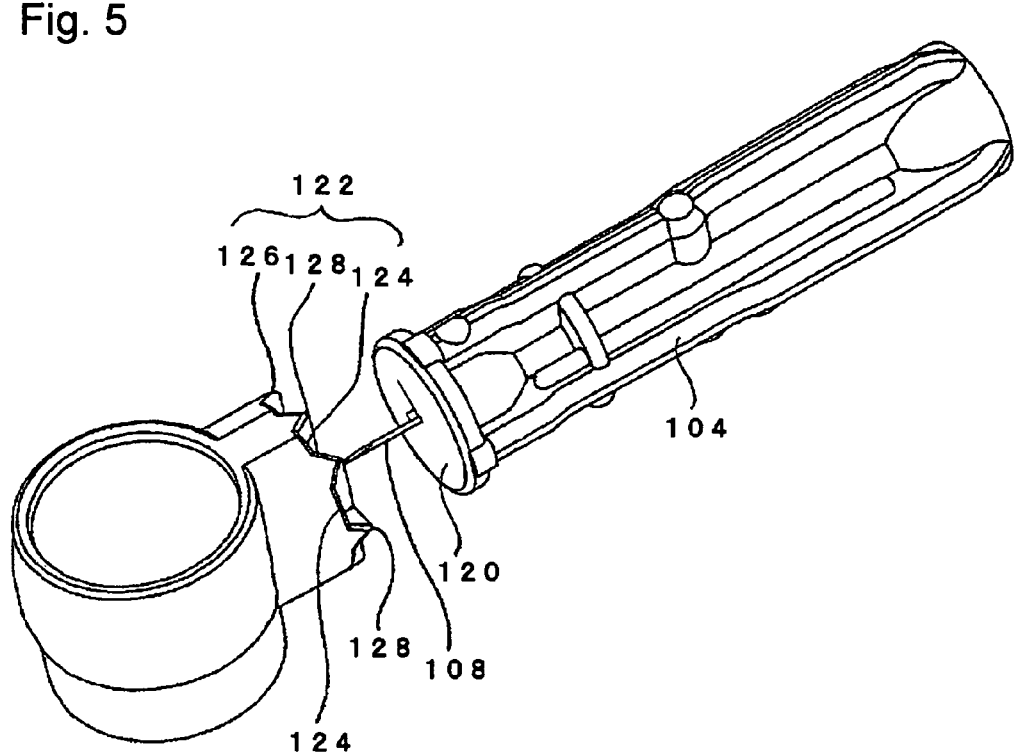
FIG. 5 is a schematic perspective view of the lancet of the present invention shown in FIG. 3, with a weakened portion being broken to separate the lancet body and the cap.
Figure 6:
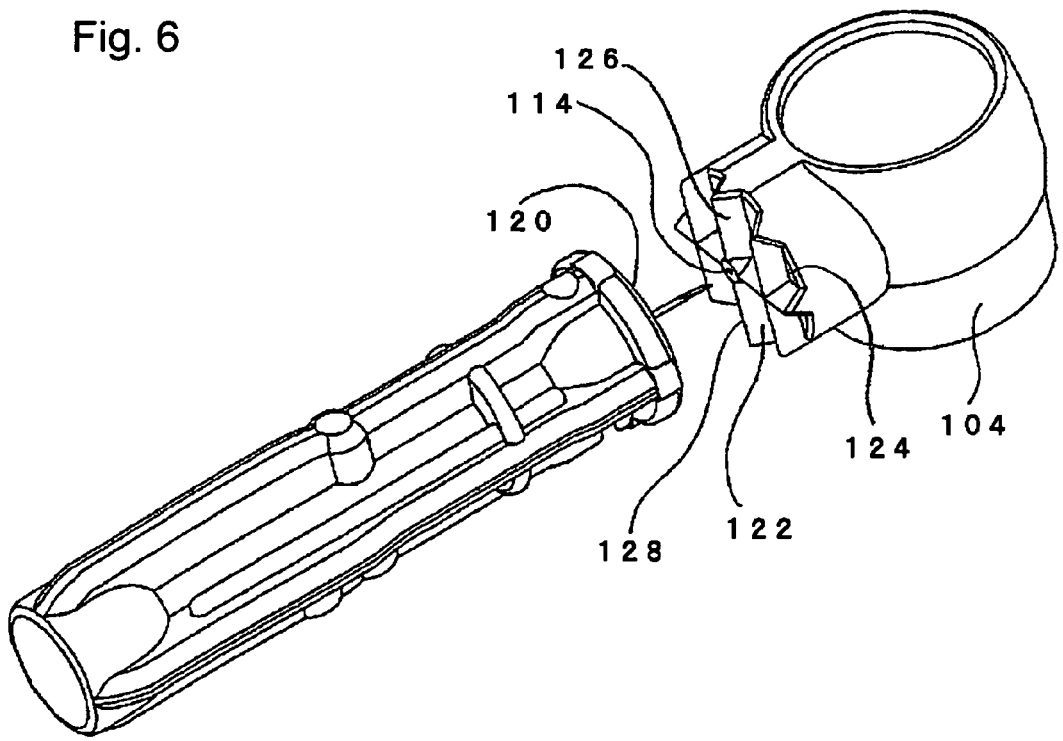
FIG. 6 is a schematic perspective view similar to FIG. 5, viewed in a direction opposite to that of FIG. 5.

The state of the distal end portion 108 of the puncturing member being exposed as described above is schematically shown in perspective views of FIG. 5 and FIG. 6. FIG. 5 shows as viewed in the same direction as in FIG. 4, and FIG. 6 shows as viewed in the opposite direction. As will be easily understood from these drawings, the end face 120 at the front end portion 112 of the lancet body 102 and end face 122 at the rear end portion 110 of the cap 104 oppose each other and the end face 120 is a flat surface in the embodiment shown.

The end face 122 has a protrusion 126 that protrudes from the base 124, and the protrusion defines a top end 128 at the distal end thereof. In the embodiment shown, the protrusion is constituted from three parallel straight ridges and one ridge that cross the former at right angles. The ridges have cross section of equilateral triangular shape in a direction perpendicular to the longitudinal direction of the ridge. Each of the ridges corresponds to a form of triangular roof or a triangular prism lying on the side thereof.

In the embodiment shown, one side of each of the ridges (the side that defines the highest portion of the ridge) defines the straight top ends of the protrusions that in turn define the imaginary plane. In other words, all of these sides lie on the imaginary plane. Since the rear end portion 110 of the cap 104 and the front end portion 112 of the lancet body 102 are in adjoining state with each other, the imaginary plane is a flat surface that substantially makes contact with the end face 120 at the front end portion 112 of the lancet body 102 in adjoining state, and such an imaginary plane is substantially the same as the end face 120.

In the lancet of the present invention, the top end 128 described above is integrally connected with the end face 120 at the front end portion 112 of the lancet body 102, so that the linkage 130 is formed between the lancet body 102 and the cap 104. In the lancet of the embodiment shown in the drawing, the weakened portion 114 and the linkage 130 are formed integrally with each other, as will be understood from FIG. 1. The linkage 130 of such a form can be made by preparing a die in such a way as the lancet can be formed with the top end 128 being linearly connected to the end face 120 of the front end portion 112 of the lancet body 102. In another embodiment, such a linear connection may be a planar connection of very small width.

As a result, in case both the imaginary plane and the end face 120 extend at right angles to the longitudinal direction of the puncturing member 106, even when the lancet body 102 and the cap 104 are twisted in directions opposite to each other around the longitudinal direction of the lancet, these members turn in the state of the imaginary plane making contact with the end face 120, and therefore angular positions of the lancet body and the cap 104 with respect to the puncturing member 106 remain substantially the same. Thus no substantial force is exerted to bend the distal end portion 108 of the puncturing member when the weakened portion 114 is broken, and therefore the distal end portion 108 of the puncturing member can be prevented from being exposed from the front end portion 120 of the lancet body 102 in a bent state.

Figure 7:
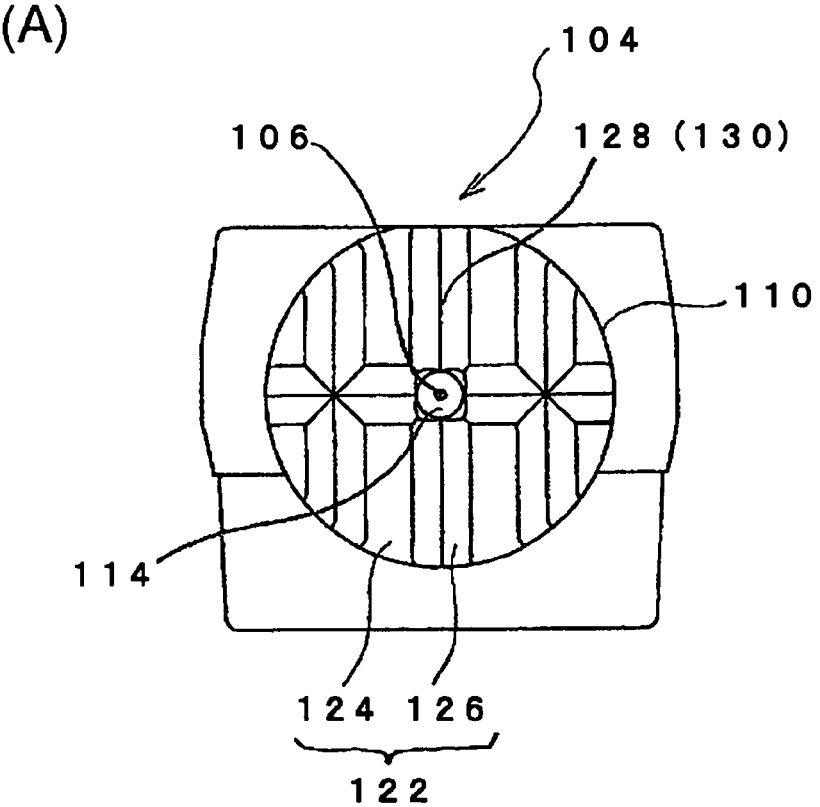
FIG. 7(A) is a schematic front view of a lancet of the present invention showing an example of end face at the rear end portion of the cap.
FIG. 7(B) is a schematic side view thereof.
Figure 7:
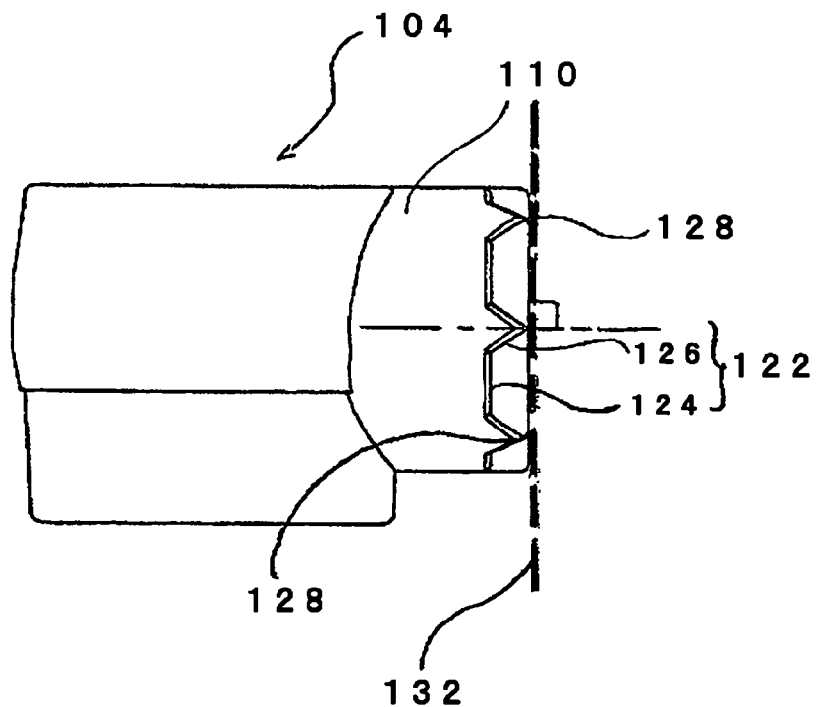

The cap 104 (in the state of being separated from the lancet body after breaking the weakened portion) of the lancet of the present invention shown in FIG. 3 to FIG. 6 is shown in front view of FIG. 7(A) as viewed in the puncturing direction, and in side view of FIG. 7(B) as viewed sideways offset from the puncturing direction.

As will be seen from FIG. 7(A), the end face 122 at the rear end portion of the cap 104 is constituted from the base 124 and the protrusion 126 that protrudes from the former. The highest portion of the protrusion 126 defines the top end 128. The protrusion shown in the drawing is constituted from three parallel ridges and one ridge that crosses the former at right angles. The straight top ends of these ridges define the imaginary plane, and the imaginary plane extends so as to include the top ends. In the embodiment shown, the straight line at the center of the ridge corresponds to the top end 128 of the protrusion 126.

The imaginary plane 132 is indicated by dashed line in FIG. 7(B). The imaginary plane has no thickness, but is indicated with a thick line to help understanding. In the lancet of the present invention shown in FIG. 3 to FIG. 6, the lancet body 102 and the cap 104 are in adjoining state, and therefore the flat surface 120 defined by the end face at the front end portion 112 of the lancet body 102 and the imaginary plane 132 overlap with each other.

As shown in FIG. 7(A), the end face 122 at rear end portion 110 of the cap 104 also has the weakened portion 114 that surrounds a part of puncturing member 106. In the embodiment shown, the weakened portion 114 and the protrusion 126 are linked to each other, although these members may not necessarily be linked.

Figure 8:
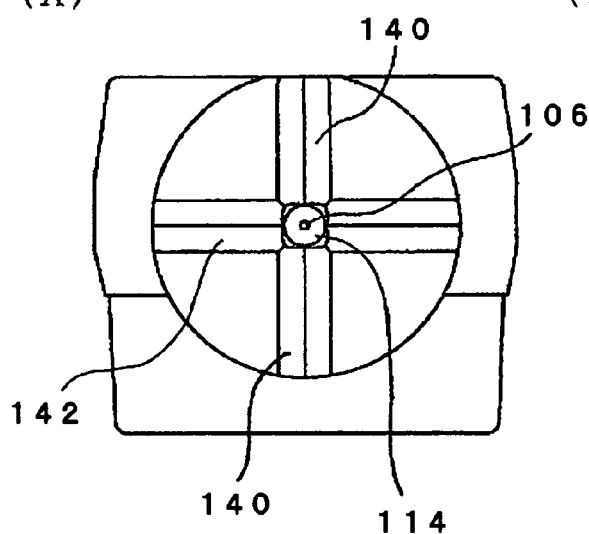
FIG. 8 is a schematic front view of a lancet of the present invention showing another embodiment of the end face at the rear end portion of the cap.
Figure 8:
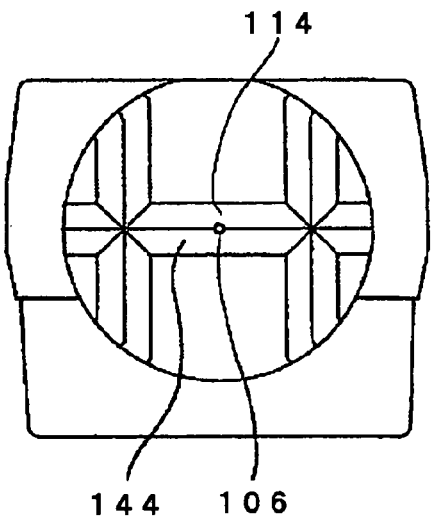
Figure 8:
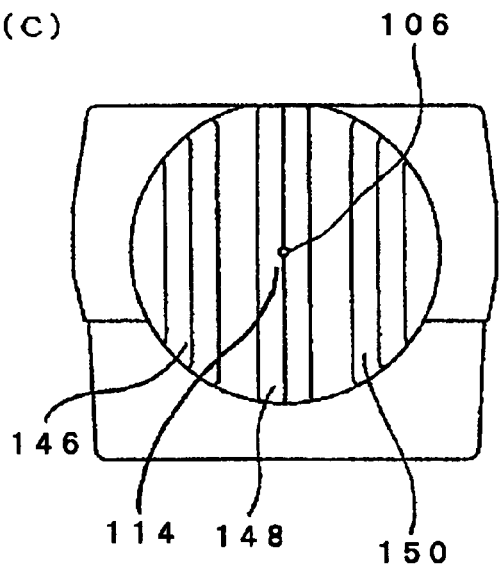
Figure 8:
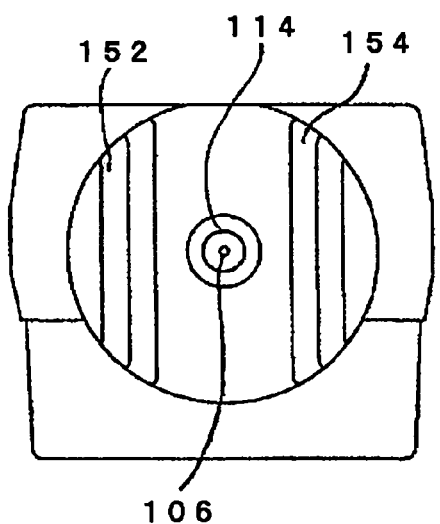

FIG. 8 shows other examples of various possible embodiments of the protrusion. In any of these drawings, the protrusion is constituted by combining straight ridges, and is schematically shown in a front view as the cap 104 is viewed in the puncturing direction similarly to FIG. 7(A).

In the embodiment shown in FIG. 8(A), straight ridges 140 and 142 cross perpendicularly at the weakened portion 114 that is disposed at the center, while surrounding the puncturing member 106. In the embodiment shown in FIG. 8(B), one ridge perpendicularly crosses two ridges that extend parallel to each other, that corresponds to the lancet shown in FIG. 3 with the ridge located at the center among the three ridges is omitted. In this embodiment, the weakened portion 114 is integrated with the ridge 144 of the protrusion, and there is no clear distinction between these members. However, it may be conceived that the periphery of the puncturing member 106 corresponds to the weakened portion 114. Accordingly, the protrusion and the weakened portion coexist also in the embodiment shown in FIG. 8(B), and this embodiment is included in the scope of the present invention.

In the embodiment shown in FIG. 8(C), three ridges 146, 148, 150 run parallel to each other as the protrusion. In this embodiment, similarly to the embodiment shown in FIG. 8(B), the weakened portion 114 is integrated with the protrusion, and there is no clear distinction between these members. In the embodiment shown in FIG. 8(D), two ridges 152 and 154 run parallel to each other as the protrusion, in a constitution corresponding to the embodiment shown in FIG. 8(C) where the ridge located at the center is omitted. In this case, however, the weakened portion 114 having the shape of independent truncated cone surrounds a part of the puncturing member 106.

In the embodiments shown in FIG. 3 to FIG. 6, the lancet body and the cap are in adjoining state. In other embodiments of the lancet of the present invention, these members may be in substantially adjoining state. In this case, the top end 128 of the protrusion is disposed at a distance from the flat surface 120 defined by the end faces at the front end portion of the lancet body 102. However, in case this distance is small, the imaginary plane would not be inclined significantly in relation to the flat surface 120 when the lancet body and the cap are twisted, and therefore there occurs no significant deviation between the direction in which the distal end portion 108 of the puncturing member extends in the cap 104 and the direction in which the rest of the puncturing member extends in the lancet body 104. As a result, the distal end portion 108 may bend at the end of the lancet body, but not to a significant extent.

In another embodiment of the lancet of the present invention, the end face at the front end portion of the lancet body defines the imaginary plane, and the end face at the rear end portion of the cap defines the flat surface, in contrast to the embodiments shown in FIG. 3 to FIG. 6. The difference is only that the imaginary plane and the flat surface change their positions with each other, and it is apparent that effect similar to that mentioned in the above description of the lancet of the present invention can be expected.

In further another embodiment, both the end face at the front end portion of the lancet body and the end face at the rear end portion of the cap define the imaginary plane. As will be apparent from the above description, according to the present invention, linkage between the lancet body and the cap can be broken while the imaginary plane performs substantially the same function as that of the flat surface. Thus it is apparent that the embodiment where both end faces define the imaginary plane is expected to achieve similar effect to that of the embodiment where one of the end faces defines the imaginary plane.

The lancet of the present invention is characterized in that the rear end portion of the cap and the front end portion of the lancet body are integrated in substantially adjoining state with each other via the weakened portion, and that at least one of the end face at the front end portion of the lancet body and the end face at the rear end portion of the cap that opposes the former defines the imaginary plane, and the other end face, if any, defines the flat surface that extends at right angles to the longitudinal direction of the puncturing member. In addition to the feature described above, the lancet of the present invention may further have the features of known lancet of the prior art.

For example, the cap may have a space 200 that firmly fits with the front end portion of the lancet body where the distal end portion of the puncturing member protrudes and houses the distal end portion of the puncturing member after the lancet has been used. This configuration makes it possible to substantially separate the distal end portion of the puncturing member after the lancet has been used. The fitting is preferably shrink fitting or snap fitting.

It is also preferable that the space 200 has an opening end 202 for inserting the front end portion of the lancet body into the space and a closed end 204 that opposes therewith. In this case, it is particularly preferable that at least the foremost part of the distal end portion of the puncturing member penetrates the wall that constitutes the closed end. Separation of the distal end portion of the puncturing member after use is made complete by providing the closed end 204.

For the lancet of the present invention and the method for manufacturing the same, technical details of the conventional lancet and the method for manufacturing the conventional lancet can be applied.

According to the lancet of the present invention, since the distal end portion of the puncturing member is suppressed from bending at the end of the lancet body when the distal end portion of the puncturing member is exposed, the lancet that reduces the pain of penetration can be provided.

The present application claims priority on Japanese Patent Application No. 2006-042340 filed on Feb. 20, 2006 (Titled of the Invention: LANCET), the disclosure of which is incorporated by reference herein.

The invention claimed is:
1. A lancet comprising:
a lancet body having a front end;
a puncturing member arranged such that a distal end portion of the puncturing member protrudes from the front end of the lancet body; and
a cap that houses and protects the distal end portion of the puncturing member before use,
wherein a front end portion of the lancet body and a rear end of the cap are integrated in a substantially adjoining state with each other via a weakened portion,
one of an end face at the front end portion of the lancet body and an end face at the rear end portion of the cap that opposes the end face at the front end portion of the lancet body has at least one protrusion, the at least one protrusion including at least three top ends, each of the top ends having the same height so as to define an imaginary plane that extends perpendicularly to a longitudinal direction of the puncturing member, and
another of the end face at the front end portion of the lancet body and the end face at the rear end portion of the cap defines an entirely flat surface that extends perpendicularly to the longitudinal direction of the puncturing member.

2. The lancet according to claim 1, wherein the front end portion of the lancet body and the rear end portion of the cap are in an adjoining state.

3. The lancet according to claim 2, wherein the top ends that define the imaginary plane are connected to the end face which defines the flat surface into an integrated configuration.

4. The lancet according to claim 1, wherein the end face at the front end portion of the lancet body has the at least one protrusion which defines the imaginary plane, and the end face at the rear end portion of the cap defines the flat surface.

5. The lancet according to claim 1, wherein the end face at the front end portion of the lancet body defines the flat surface, and the end face at the rear end portion of the cap has the at least one protrusion which defines the imaginary plane.

6. The lancet according to claim 1, wherein the end face at the front end portion of the lancet body has the at least one protrusion which defines the imaginary plane as a first imaginary plane, and the end face at the rear end portion of the cap defines a second imaginary plane as the flat surface.

7. The lancet according to claim 1, wherein the at least one protrusion has a shape of a ridge.

8. The lancet according to claim 1, wherein the at least one protrusion comprises a plurality of parallel ridges and one ridge that crosses the parallel ridges at right angles.

9. The lancet according to claim 1, wherein the puncturing member has a diameter not larger than 0.4 mm.

10. The lancet according to claim 1, wherein the lancet is manufactured from a resin by insertion molding in which the puncturing member is inserted in the resin.

11. The lancet according to claim 1, wherein the height of the at least three top ends is a maximum height of the at least one protrusion.

\* \* \* \* \*